(12) United States Patent
Yamada

(10) Patent No.: US 12,062,447 B2
(45) Date of Patent: Aug. 13, 2024

(54) MEDICAL IMAGE DIAGNOSIS SUPPORT DEVICE, METHOD, AND PROGRAM

(71) Applicant: FUJIFILM Corporation, Tokyo (JP)

(72) Inventor: Kenta Yamada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 629 days.

(21) Appl. No.: 17/210,517

(22) Filed: Mar. 24, 2021

(65) Prior Publication Data

US 2021/0210206 A1    Jul. 8, 2021

Related U.S. Application Data

(63) Continuation of application No. PCT/JP2019/022054, filed on Jun. 3, 2019.

(30) Foreign Application Priority Data

Sep. 27, 2018    (JP) .................................. 2018-182734

(51) Int. Cl.
| | |
|---|---|
| *G16H 50/20* | (2018.01) |
| *G06T 7/00* | (2017.01) |
| *G16H 30/20* | (2018.01) |
| *G16H 30/40* | (2018.01) |

(52) U.S. Cl.
CPC ........... *G16H 50/20* (2018.01); *G06T 7/0012* (2013.01); *G16H 30/20* (2018.01); *G16H 30/40* (2018.01); *G06T 2207/30004* (2013.01)

(58) Field of Classification Search
CPC ........ G16H 50/20; G16H 30/20; G16H 30/40; G06T 7/0012; G06T 2207/30004

USPC .......................................................... 382/128
See application file for complete search history.

(56) References Cited

U.S. PATENT DOCUMENTS

| | | | |
|---|---|---|---|
| 9,144,407 B2 | 9/2015 | Nakamura | |
| 10,013,727 B2* | 7/2018 | Iwase | ..................... G16H 15/00 |
| 10,198,825 B2* | 2/2019 | Ward | ..................... A61B 6/032 |
| 10,552,672 B2* | 2/2020 | Iwase | ..................... G16H 30/20 |
| 11,250,603 B2* | 2/2022 | Utsunomiya | ............. G06T 7/33 |
| 2003/0063785 A1 | 4/2003 | Oosawa | |
| 2004/0024292 A1 | 2/2004 | Menhardt et al. | |

(Continued)

FOREIGN PATENT DOCUMENTS

| | | |
|---|---|---|
| JP | 2002253539 | 9/2002 |
| JP | 2003010166 | 1/2003 |

(Continued)

OTHER PUBLICATIONS

"Office Action of Japan Counterpart Application", issued on Jul. 5, 2022, with English translation thereof, pp. 1-8.

(Continued)

*Primary Examiner* — William D Titcomb
(74) *Attorney, Agent, or Firm* — JCIPRNET

(57) ABSTRACT

The medical image diagnosis support device includes an image reception unit, an information reception unit that receives information corresponding to the received image, an extraction unit that extracts one or more applications corresponding to the received information and analyzing the received image, an activation unit that activates at least one of the extracted applications, and a display control unit that displays, in a case where a result of analysis executed in the past by the activated application exists for the received image, the result of analysis on a display unit.

11 Claims, 6 Drawing Sheets

(56) References Cited

U.S. PATENT DOCUMENTS

| | | | |
|---|---|---|---|
| 2015/0086092 A1 | 3/2015 | Itada et al. | |
| 2015/0235613 A1* | 8/2015 | Yamada | G06T 7/0012 |
| | | | 345/589 |
| 2015/0331995 A1* | 11/2015 | Zhao | G16H 50/20 |
| | | | 705/2 |
| 2015/0347682 A1* | 12/2015 | Chen | G16H 50/20 |
| | | | 705/2 |
| 2015/0356245 A1* | 12/2015 | Kozuka | G16H 50/70 |
| | | | 705/2 |
| 2016/0035071 A1* | 2/2016 | Yamada | A61B 6/032 |
| | | | 345/647 |
| 2016/0086049 A1* | 3/2016 | Yamada | G06T 11/60 |
| | | | 382/199 |
| 2016/0364862 A1* | 12/2016 | Reicher | G16H 50/50 |
| 2017/0091413 A1* | 3/2017 | Kondo | G16H 50/20 |
| 2017/0360285 A1* | 12/2017 | Yamada | A61B 1/0005 |
| 2018/0082159 A1 | 3/2018 | Torii | |
| 2018/0144828 A1* | 5/2018 | Baker | G16H 30/40 |
| 2018/0185101 A1* | 7/2018 | Yamada | A61B 34/20 |
| 2018/0225884 A1* | 8/2018 | Yamada | G06T 7/149 |
| 2018/0226143 A1* | 8/2018 | Khashman | G06F 16/254 |
| 2018/0243034 A1* | 8/2018 | Yamada | A61B 5/004 |
| 2021/0022662 A1* | 1/2021 | Hyun | G16H 30/20 |

FOREIGN PATENT DOCUMENTS

| | | |
|---|---|---|
| JP | 2004252971 | 9/2004 |
| JP | 2005533578 | 11/2005 |
| JP | 2008253681 | 10/2008 |
| JP | 2009005906 | 1/2009 |
| JP | 2011011069 | 1/2011 |
| JP | 2013149117 | 8/2013 |
| JP | 2015085182 | 5/2015 |
| JP | 2018047571 | 3/2018 |

OTHER PUBLICATIONS

"Office Action of Japan Counterpart Application", issued on Dec. 14, 2021, with English translation thereof, p. 1-p. 9.

"International Search Report (Form PCT/ISA/210) of PCT/JP2019/022054," mailed on Aug. 13, 2019, with English translation thereof, pp. 1-5.

"Written Opinion of the International Searching Authority (Form PCT/ISA/237) of PCT/JP2019/022054," mailed on Aug. 13, 2019, with English translation thereof, pp. 1-13.

\* cited by examiner

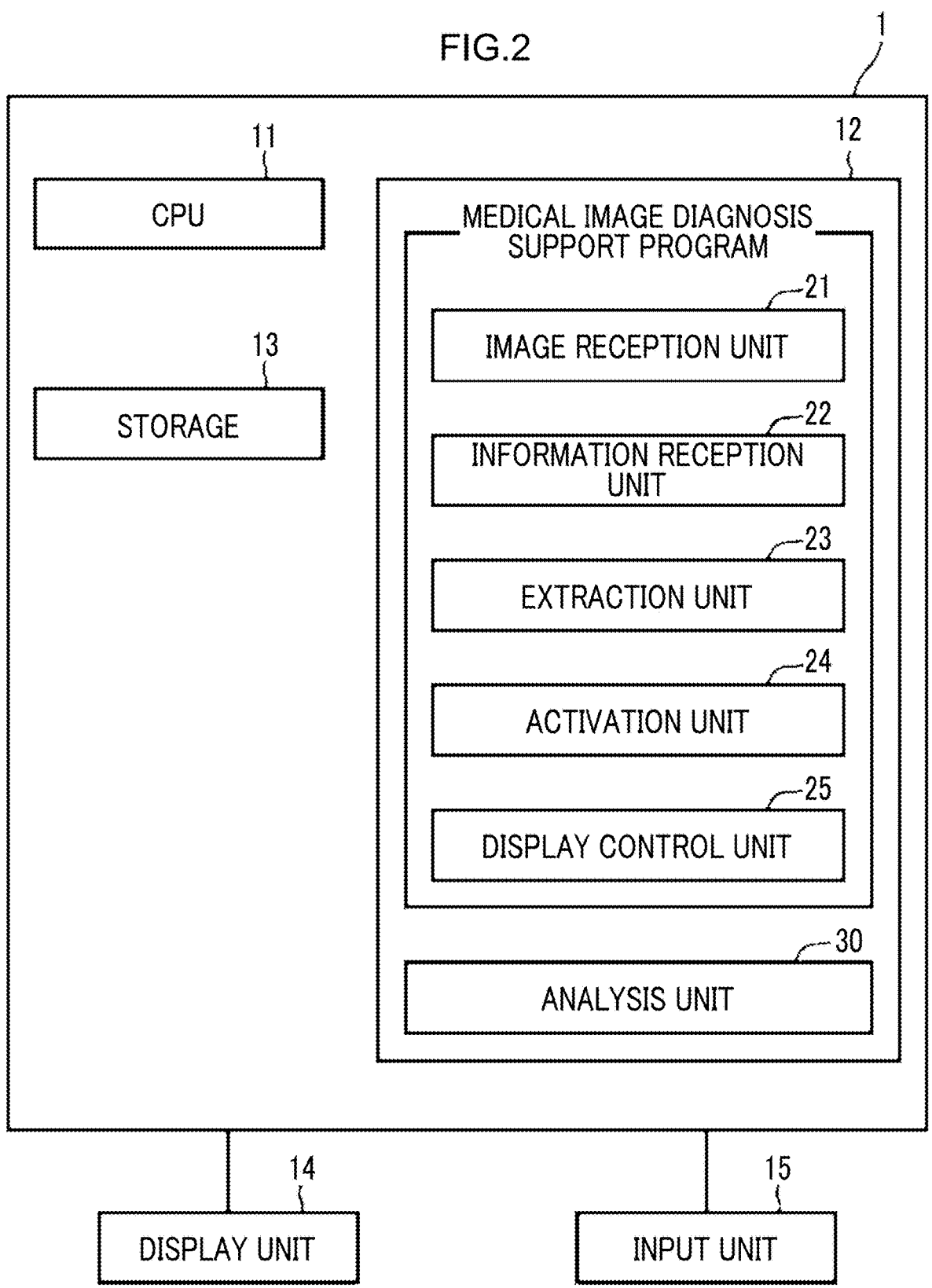

FIG.3

| IMAGE INFORMATION | ANALYSIS APPLICATION |
|---|---|
| HEAD IMAGE | DENTITION OBSERVATION APPLICATION |
| HEAD IMAGE (WITH CONTRAST) | CEREBRAL BLOOD VESSEL SHAPE AND BLOOD FLOW ANALYSIS APPLICATION |
| HEART IMAGE (WITHOUT CONTRAST) | CALCIFICATION SCORE CALCULATION APPLICATION |
| HEART IMAGE (WITH CONTRAST) | HEARTBEAT FUNCTION, CARDIOVASCULAR (CORONARY ARTERY), AND MYOCARDIAL BLOOD FLOW FUNCTION ANALYSIS APPLICATION |
| HEART IMAGE | CALCIFICATION SCORE CALCULATION APPLICATION<br>CARDIAC FUNCTION ANALYSIS APPLICATION<br>CORONARY ARTERY ANALYSIS APPLICATION |
| LUNG FIELD IMAGE | LUNG PROPERTY, SHAPE, AND BRONCHIAL SHAPE ANALYSIS APPLICATION |
| LUNG FIELD IMAGE (WITH PLURALITY OF PHASE INPUTS) | RESPIRATORY FUNCTION ANALYSIS APPLICATION |
| LUNG FIELD IMAGE | SURGERY SIMULATION ANALYSIS APPLICATION |
| ABDOMINAL IMAGE | LIVER, KIDNEY, AND SPLEEN SIZE ANALYSIS APPLICATION |
| ABDOMINAL IMAGE (WITH CONTRAST) | SURGERY |
| ALL IMAGES | BONE AND MUSCLE SHAPE ANALYSIS APPLICATION |
| ALL IMAGES | JOINT STATE ANALYSIS APPLICATION |
| ALL IMAGES (WITH CONTRAST) | BLOOD VESSEL SHAPE ANALYSIS APPLICATION |

MEDICAL IMAGE DIAGNOSIS SUPPORT DEVICE, METHOD, AND PROGRAM

CROSS-REFERENCE TO RELATED APPLICATION

The present application is a continuation application of International Application No. PCT/JP2019/022054, filed Jun. 3, 2019, which claims priority to Japanese Patent Application No. 2018-182734, filed Sep. 27, 2018. The contents of these applications are incorporated herein by reference in their entirety.

BACKGROUND

Field of the Invention

The present disclosure relates to a medical image diagnosis support device, method, and program.

Related Art

In recent years, advances in medical instruments such as a computed tomography (CT) device, an ultrasonic (US) diagnostic device, a magnetic resonance imaging (MRI) device, a positron emission tomography (PET) device, and a single-photon emission computed tomography (SPECT) device, in addition to an X-ray imaging device, have made it possible to perform image diagnosis using a high-resolution three-dimensional medical image with higher quality. In particular, since a region of a lesion can be accurately specified by the image diagnosis using the three-dimensional medical image, appropriate treatment has been performed based on the specified result. In addition, analysis on the three-dimensional medical image is performed by various analysis applications to extract a region, position, and volume of a lesion included in the medical image, and these are acquired as results of analysis. The results of analysis generated by analysis processing in this manner are associated with examination information, such as name, gender, and age of a patient, and modality from which the medical image has been acquired, and stored in a database for diagnosis.

On the other hand, recent image diagnostic device can be roughly divided into an image reading viewer for reading a medical image and an analysis workstation for performing detailed analysis on the medical image. In many cases, a user, such as an image reading doctor and a doctor, confirms the presence or absence of a disease by the image reading viewer and performs detailed analysis on the detected disease by the analysis workstation, thereby collecting information for more accurate diagnosis.

In actual operation, the user selects an image to be read, and then the user selects an analysis application to be activated in the analysis workstation. However, since there are many analysis applications depending on a system of the analysis workstation, there is a problem that it takes time and effort to find the analysis application to be activated, or the analysis application is not selected properly. In some cases, the workflow is degraded due to these problems.

In general, the application to be executed for one case is fixed. Therefore, JP2011-011069A discloses a technique in which, in a case of displaying a three-dimensional image, an analysis application that analyzes the three-dimensional image is specified according to a part included in the three-dimensional image, and only a menu for selecting the specified analysis application is displayed on a display unit.

In addition, JP2008-253681A discloses a technique of detecting an abnormal part existing in a medical image by referring to a database based on an acquired first predetermined condition and selecting and activating a corresponding abnormal part detection application. In addition, JP2005-533578A discloses a technique of selecting one acquisition model from a plurality of acquisition models based on attributes of a digital image, and selecting and executing a computer-aided design (CAD) application from a plurality of CAD applications by using the selected acquisition model.

On the other hand, in a case where an analysis application is executed for an image to be read, it may take time to analyze the image, and it is desired to reduce the time required for the analysis.

SUMMARY

The present disclosure has been made in view of the above circumstances, and an object thereof is to shorten the time required for analysis.

A medical image diagnosis support device of the present disclosure comprises: an image reception unit that receives an image; an information reception unit that receives information corresponding to the image received by the image reception unit; an extraction unit that extracts one or more applications corresponding to the information received by the information reception unit and analyzing the image received by the image reception unit; an activation unit that activates at least one of the applications extracted by the extraction unit; and a display control unit that displays, in a case where a result of analysis executed in the past by the application activated by the activation unit exists for the image received by the image reception unit, the result of analysis on a display unit.

In the medical image diagnosis support device of the present disclosure, the display control unit may display the result of analysis executed by the application activated by the activation unit on the display unit.

In the medical image diagnosis support device of the present disclosure, the display control unit may display information indicating the application activated by the activation unit on the display unit.

In the medical image diagnosis support device of the present disclosure, the display control unit may display information indicating the application extracted by the extraction unit on the display unit.

In the medical image diagnosis support device of the present disclosure, in a case where a plurality of the applications are extracted by the extraction unit, the display control unit may display, on the display unit, information indicating a predetermined number of applications selected from the plurality of applications based on priorities.

In the medical image diagnosis support device of the present disclosure, in a case where a plurality of the applications are extracted by the extraction unit, the activation unit may activate a predetermined number of applications selected from the plurality of applications based on priorities.

In the medical image diagnosis support device of the present disclosure, the information received by the information reception unit may include at least one of information indicating a designated region in a reception image which is the image received by the image reception unit, information for recognizing each part of the reception image, information for recognizing each organ region of the reception image, DICOM tag information, or information about a past report.

In the medical image diagnosis support device of the present disclosure, in a case where an input instruction is made on a reception image which is the image received by the image reception unit, the extraction unit may extract the application based on information about the reception image on which the input instruction is made, and in a case where an input instruction is made on a designated region in the reception image, the extraction unit may extract the application based on information about a part in the designated region on which the input instruction is made.

In the medical image diagnosis support device of the present disclosure, the image received by the image reception unit may be a medical image.

A medical image diagnosis support method of the present disclosure comprises: receiving an image; receiving information corresponding to the received image; extracting one or more applications corresponding to the received information and analyzing the received image; activating at least one of the extracted applications; and displaying, in a case where a result of analysis executed in the past by the activated application exists for the received image, the result of analysis on a display unit.

A program for causing a computer to execute the medical image diagnosis support method according to the present disclosure may be provided.

Another medical image diagnosis support device according to the present disclosure comprises: a memory that stores an instruction to be executed by a computer; and a processor configured to execute the stored instruction, in which the processor executes processing of receiving an image, receiving information corresponding to the received image, extracting one or more applications corresponding to the received information and analyzing the received image, activating at least one of the extracted applications, and displaying, in a case where a result of analysis executed in the past by the activated application exists for the received image, the result of analysis on a display unit.

According to the medical image diagnosis support device, method, and program of the present disclosure, the time required for analysis can be shortened.

BRIEF DESCRIPTION OF THE DRAWINGS

FIG. 2 is a schematic block diagram showing a configuration of the medical image diagnosis support device according to the embodiment of the present disclosure.

FIG. 3 is a diagram showing an example of a table used in the embodiment of the present disclosure.

DETAILED DESCRIPTION

Figure 1:
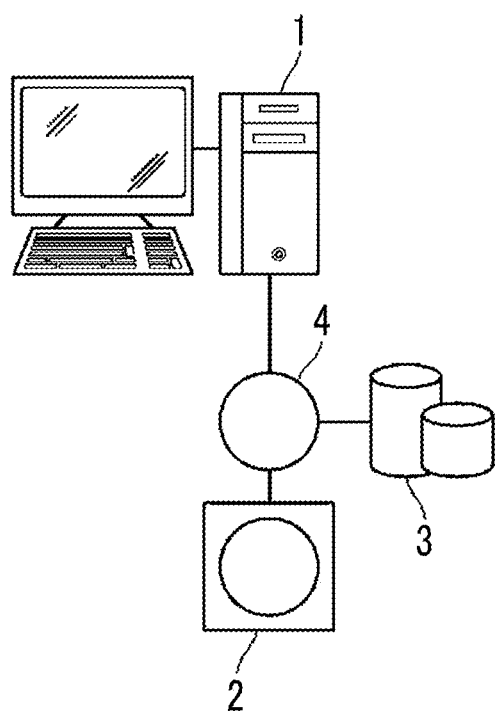
FIG. 1 is a hardware configuration diagram showing an outline of a diagnosis support system to which a medical image diagnosis support device according to an embodiment of the present disclosure is applied.

Hereinafter, an embodiment of the present disclosure will be described with reference to the drawings. FIG. 1 is a hardware configuration diagram showing an outline of a diagnosis support system to which a medical image diagnosis support device according to an embodiment of the present disclosure is applied. As shown in FIG. 1, in the diagnosis support system, a medical image diagnosis support device 1, a three-dimensional image capturing device 2, and an image storage server 3 according to the present embodiment are connected in a communicable state via a network 4.

The three-dimensional image capturing device 2 is a device that generates a three-dimensional image showing a part, which is a diagnosis target of a subject, by imaging the part, and is specifically a CT device, an MM device, a PET device, and the like. A medical image generated by the three-dimensional image capturing device 2 is transmitted to the image storage server 3 and stored.

The image storage server 3 is a computer that stores and manages various pieces of data, and comprises a large-capacity external storage device and database management software. The image storage server 3 communicates with other devices via a wired or wireless network 4 to transmit and receive image data and the like. Specifically, various pieces of data including image data of the three-dimensional image generated by the three-dimensional image capturing device 2 and accessory information are acquired via a network and stored in a recording medium such as a large-capacity external storage device for management.

The accessory information includes, for example, an image ID for identifying an individual medical image, a patient identification (ID) for identifying a subject, an examination ID for identifying an examination, a unique identification (UID) assigned to each medical image, an examination date and time at which each medical image is generated, a type of modality used in an examination to acquire each medical image, patient information, such as name, age, and gender of a patient, an examination part (imaging part), imaging information (imaging protocol, imaging sequence, imaging method, imaging conditions, use of contrast agent, and the like), and information, such as a series number or a collection number in a case where a plurality of medical images are acquired in one examination. In addition, a medical image is analyzed by an analysis unit 30 described below to extract a region, position, and volume of a lesion included in the medical image, and information indicating the results of analysis is also used as accessory information. The result of analysis is associated with each analysis application of the analysis unit 30.

The storage format of the image data and the communication between the devices via the network 4 are based on a protocol such as digital imaging and communication in medicine (DICOM). In a case where the image storage server 3 receives a browsing request from the medical image diagnosis support device 1 via the network 4, the image storage server 3 retrieves a registered medical image and transmits the retrieved medical image to the medical image diagnosis support device 1 as a request source.

In the medical image diagnosis support device 1, a medical image diagnosis support program of the present disclosure is installed in one computer. The computer may be a workstation or personal computer directly operated by a doctor who makes diagnosis, or may be a server computer connected to them via a network. A medical image diagnosis support program is recorded on a recording medium such as a digital versatile disc (DVD) or a compact disc read only memory (CD-ROM), distributed, and is installed in a computer from the recording medium. Alternatively, the program is stored in a storage device of a server computer connected to a network or a network storage in an externally accessible state, and is downloaded and installed in a computer used by a doctor in response to a request.

FIG. 2 is a diagram showing a schematic configuration of the medical image diagnosis support device which is the embodiment of the present disclosure realized by installing a medical image diagnosis support program in a computer. As shown in FIG. 2, the medical image diagnosis support device 1 comprises a central processing unit (CPU) 11, a memory 12, and a storage 13 as a standard workstation configuration. In addition, a display unit 14 including a liquid crystal display or the like, and an input unit 15 including a keyboard, a mouse, or the like are connected to the medical image diagnosis support device 1. The input unit 15 receives various setting inputs by a user. The display unit 14 and the input unit 15 may be used in common by using a touch panel.

The storage 13 includes a hard disk drive, a solid state drive (SSD), and the like. The storage 13 stores a medical image of the subject acquired from the image storage server 3 via the network 4 and various pieces of information including information required for processing.

The memory 12 stores a medical image diagnosis support program. The medical image diagnosis support program specifies, as processing to be executed by the CPU 11: image reception processing of receiving an image; information reception processing of receiving information corresponding to the received image; extraction processing of extracting one or more analysis applications corresponding to the received information and analyzing the received image; activation processing of activating at least one of the extracted analysis applications; and display control processing of displaying, in a case where a result of analysis executed in the past by the activated analysis application exists for the received image, the result of analysis on a display unit. The analysis application corresponds to the application of the present disclosure.

Then, in a case where the CPU 11 executes these kinds of processing according to the program, the computer functions as an image reception unit 21, an information reception unit 22, an extraction unit 23, an activation unit 24, and a display control unit 25.

The memory 12 stores the analysis unit 30 that analyzes a medical image by a plurality of analysis applications. The analysis unit 30 comprises a plurality of analysis applications for performing various analysis processes instructed by a user. In the present embodiment, the analysis unit 30 is provided in the medical image diagnosis support device 1, but the technique of the present disclosure is not limited to this, and the analysis unit 30 may be provided in an external instrument other than the medical image diagnosis support device 1.

The image reception unit 21 receives an image (hereinafter, referred to as a target image) to be subjected to image diagnosis. Specifically, in a case where a user such as an image reading doctor and a doctor performs an operation requesting browsing of a target image by using the input unit 15, a browsing request is transmitted to the image storage server 3, and the image reception unit 21 receives the target image retrieved and transmitted by the image storage server 3.

The information reception unit 22 receives information corresponding to the target image received by the image reception unit 21. The information received by the information reception unit 22 includes at least one of information indicating a designated region in the target image, information for recognizing each part of the target image, information for recognizing each organ region of the target image, DICOM tag information, or information about a past report. The target image corresponds to the reception image of the present disclosure.

The information indicating the designated region in the target image is pixel data and voxel data of the designated region designated by a user using the input unit 15, specifically, a point region, a region of interest (ROI), and a volume of interest (VOI). As an example, in a case where a blood vessel in a heart region is designated as an ROI by a user, the information reception unit 22 receives pixel data (pixel value) of the designated ROI. As another example, in a case where a kidney region is designated as a VOI by a user, the information reception unit 22 receives voxel data of the designated VOI.

The information for recognizing each part of the target image is information for recognizing a part of a subject included in the target image, and the information reception unit 22 receives information about an imaging part included in the accessory information registered together with the target image as the information for recognizing each part of the target image. The technique of the present disclosure is not limited to this. As an example, the information reception unit 22 may normalize a plurality of tomographic images constituting the target image, input a feature amount calculated for each normalized tomographic image to a classifier obtained by an AdaBoost method to calculate a score, for each part, indicating a likelihood of being the part, and receive a part with the calculated highest score as information about a part of a subject. In addition, as an example, the information reception unit 22 may receive information about a part recognized by using a method based on color template matching (see, for example, JP2002-253539A), a method using a unique image of each part (see, for example, JP2003-010166A), and the like.

The information for recognizing each organ region of the target image is information for recognizing an organ of a subject included in the target image. Specifically, as an example, the information reception unit 22 may normalize a plurality of tomographic images constituting the target image, input a feature amount calculated for each normalized tomographic image to a classifier obtained by an AdaBoost method to calculate a score, for each organ, indicating a likelihood of being the organ, and receive an organ with the calculated highest score as organ information.

The DICOM tag information indicates accessory information regarding the target image. The information included in the accessory information is as described above, and the description thereof is omitted here.

The information about the past report is information about a report generated in the past with respect to the target image, and information such as an image ID for identifying the target image, an image reading doctor ID for identifying an image diagnosis doctor who performed image reading, a lesion name, position information of the lesion, and findings are recorded.

The extraction unit 23 extracts one or more analysis applications corresponding to the information received by the information reception unit 22 and analyzing the target image received by the image reception unit 21 from the plurality of analysis applications provided in the analysis unit 30. Specifically, the extraction unit 23 has a table in which image information indicating a part and an organ included in a three-dimensional image is associated with a type of analysis application used for analysis of the part and the organ. FIG. 3 is a diagram showing an example of a table used in the embodiment of the present disclosure. As shown in FIG. 3, in a table T, image information indicating a part and an organ is associated with a type of analysis application. Hereinafter, the analysis application may be abbreviated as an application.

In the present embodiment, the information received by the information reception unit 22 is information for recognizing each part of the target image and information for recognizing each organ region of the target image. The extraction unit 23 extracts an application corresponding to the information received by the information reception unit 22, that is, the image information of which part or organ the target image is. Specifically, as shown in FIG. 3, the extraction unit 23 extracts a dentition observation application in a case where the image information is a head image, and extracts a cerebral blood vessel shape and blood flow analysis application in a case where the image information is a head image with contrast.

Further, the extraction unit 23 respectively extracts a calcification score calculation application in a case where the image information is a heart image without contrast, a heartbeat function, cardiovascular (coronary artery), and myocardial blood flow function analysis application in a case where the image information is a heart image with contrast, a calcification score calculation application, a cardiac function analysis application, and a coronary artery analysis application in a case where the image information is a heart image. Further, the extraction unit 23 extracts at least one of a lung property, shape, and bronchial shape analysis application or a surgery simulation analysis application in a case where the image information is a lung field image, and extracts a respiratory function analysis application in a case where the image information is a lung field image with a plurality of phase inputs.

Further, the extraction unit 23 extracts a liver, kidney, and spleen size analysis application in a case where the image information is an abdominal image, and extracts a surgery simulation analysis application in a case where the image information is an abdominal image with contrast.

Further, the extraction unit 23 extracts at least one of a bone and muscle shape analysis application or a joint state analysis application for all images, and extracts a blood vessel shape analysis application for all images with contrast.

In the present embodiment, the extraction unit 23 has the table T shown in FIG. 3, but the technique of the present disclosure is not limited to this. Even though the table T is not provided, any method may be used as long as the analysis application can be derived from the information received by the information reception unit 22.

In the technique of the present disclosure, the association between the image information as the information received by the information reception unit 22 and the analysis application is not limited to the association shown in the table T shown in FIG. 3. The association can be randomly set by a user operating the input unit 15.

The activation unit 24 activates all the analysis applications extracted by the extraction unit 23. The activation unit 24 of the present embodiment activates all the analysis applications extracted by the extraction unit 23, but the technique of the present disclosure is not limited to this, and in a case where the extraction unit 23 extracts a plurality of analysis applications, the activation unit 24 need only activate at least one analysis application. In this case, the activation unit 24 activates a predetermined number of analysis applications selected from the plurality of analysis applications based on priorities. As an example, the priorities can be determined in descending order of frequency of use in the analysis unit 30.

Figure 4:
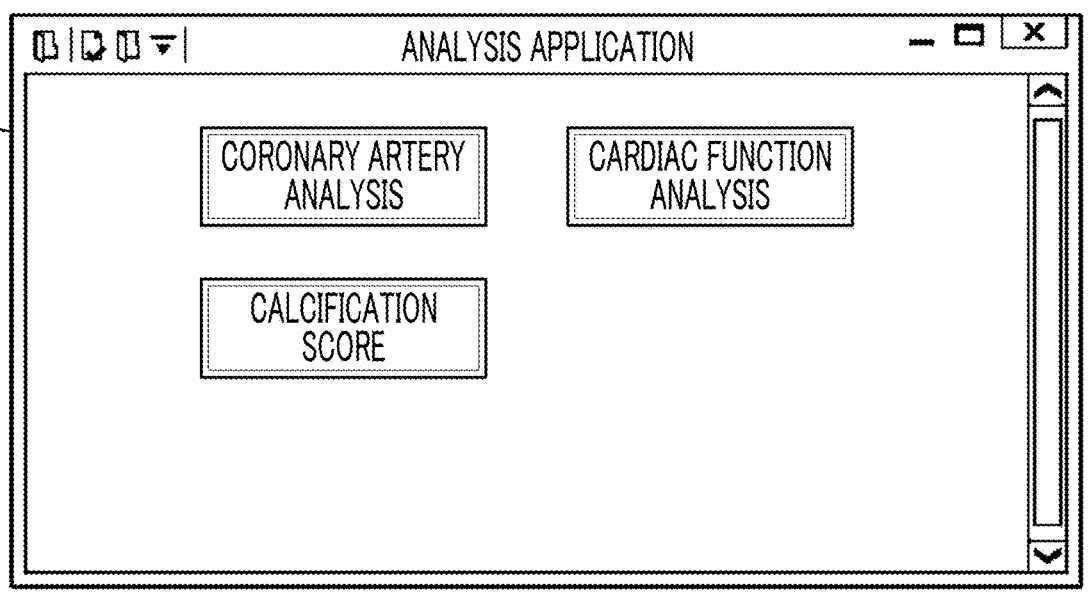
FIG. 4 is a diagram showing an example of displaying information indicating an analysis application activated in the embodiment of the present disclosure.

The display control unit 25 displays the target image received by the image reception unit 21 on the display unit 14. In addition, the display control unit 25 displays information indicating the application activated by the activation unit 24 on the display unit 14. FIG. 4 is a diagram showing an example of displaying information indicating the analysis application activated in the embodiment of the present disclosure. In a case where the information received by the information reception unit 22 is a heart image, the analysis applications extracted by the extraction unit 23 are three applications of calcification score calculation application, a cardiac function analysis application, and a coronary artery analysis application, as shown in FIG. 3. In the present embodiment, since the activation unit 24 activates all the applications extracted by the extraction unit 23, the display control unit 25 displays, as shown in FIG. 4, three pieces of information of "coronary artery analysis", "cardiac function analysis", and "calcification score" on a screen 20 of the display unit 14 as information indicating the applications activated by the activation unit 24.

In the present embodiment, the display control unit 25 displays the three pieces of information of "coronary artery analysis", "cardiac function analysis", and "calcification score" on the screen 20 of the display unit 14, but the technique of the present disclosure is not limited to this. For example, in a case where a user operates the input unit 15, the display control unit 25 may display "coronary artery analysis", "cardiac function analysis", and "calcification score" on the display unit 14 in order.

In addition, the display control unit 25 displays a result of analysis executed by the analysis application activated by the activation unit 24 on the display unit 14. In the present embodiment, the display control unit 25 displays, in a case where a result of analysis executed in the past by the analysis application activated by the activation unit 24 exists for the target image received by the image reception unit 21, the result of analysis on the display unit 14.

Specifically, the display control unit 25 retrieves accessory information about the target image, determines whether or not there is information on the result of analysis of the analysis application activated by the activation unit 24, and in a case where there is the result of analysis, the display control unit 25 displays the result of analysis on the display unit 14.

Figure 5:
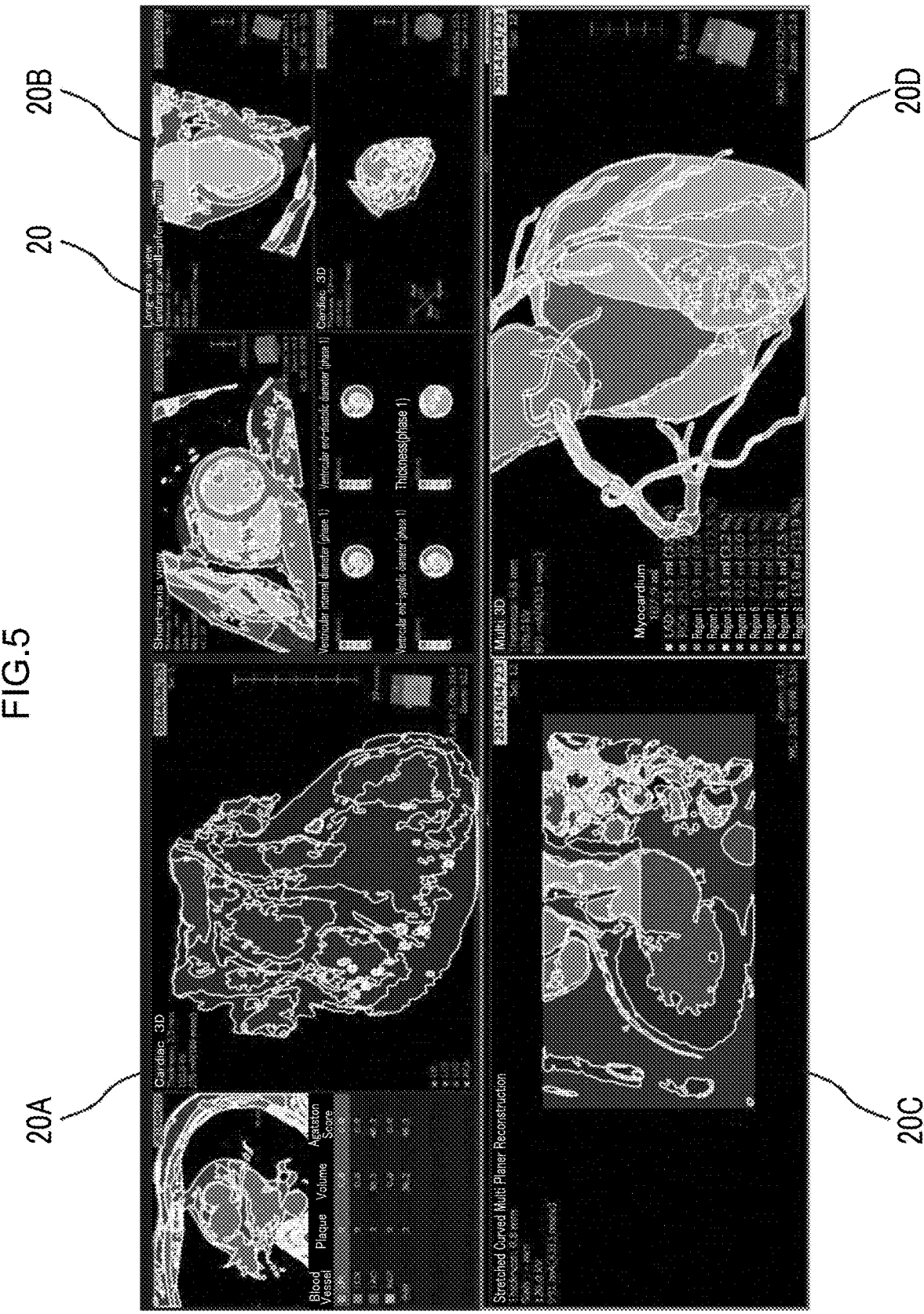
FIG. 5 is a diagram showing an example of displaying a result of analysis of the analysis application activated in the embodiment of the present disclosure.

FIG. 5 is a diagram showing an example of displaying the result of analysis of the analysis application activated in the embodiment of the present disclosure. On the screen 20 of the display unit 14, the display control unit 25 displays a result of analysis of the calcification score calculation application on an upper left screen 20A, a result of analysis of the cardiac function analysis application on an upper right screen 20B, a result of analysis (stretch curved multi planer reconstruction (CPR) image) of the coronary artery analysis application on a lower left screen 20C, and a result of analysis (multi three-dimensional image) of the coronary artery analysis application on a lower right screen 20D, respectively.

Figure 6:
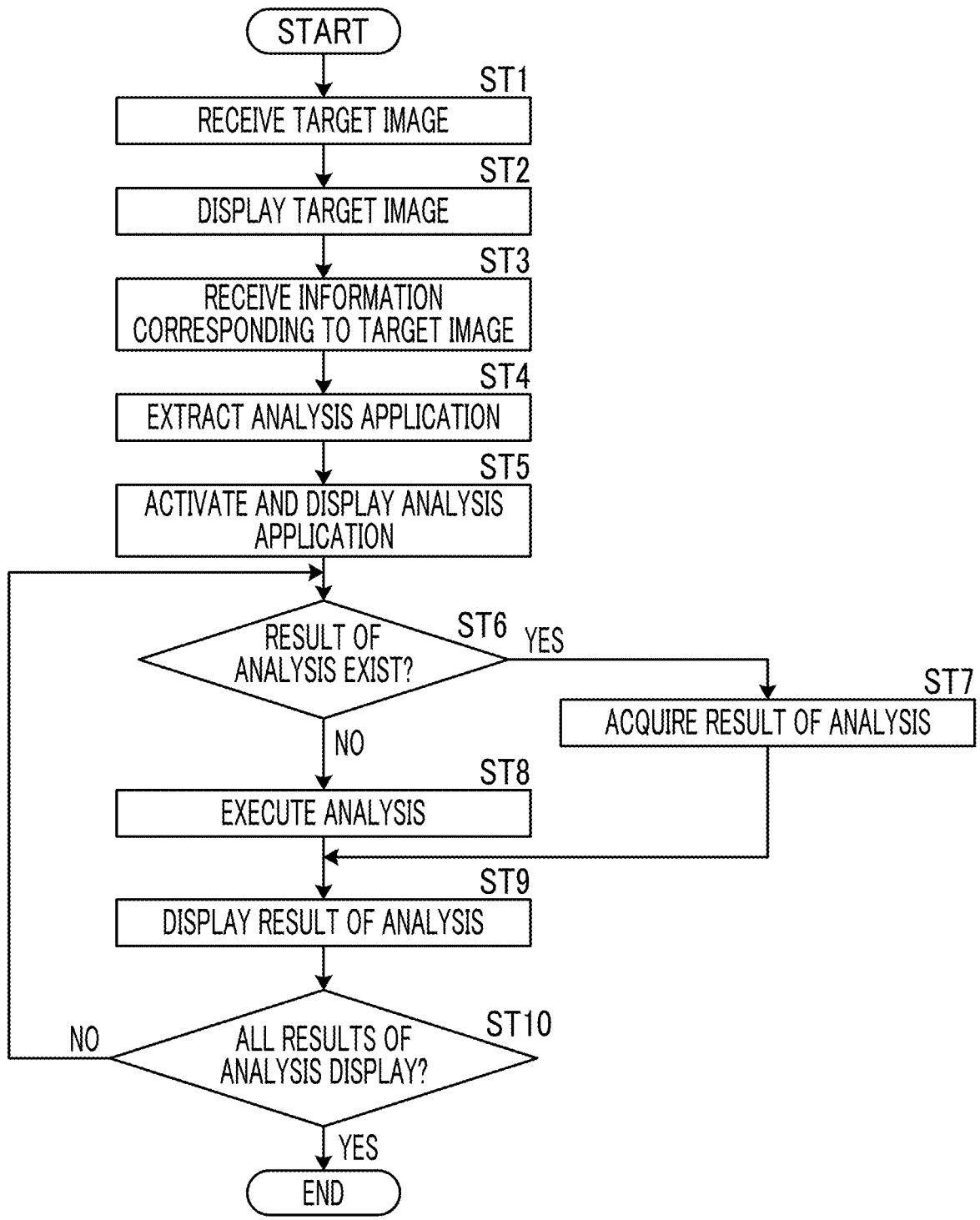
FIG. 6 is a flowchart showing medical image diagnosis support processing performed in the embodiment of the present disclosure.

Next, the processing performed in the present embodiment will be described. FIG. 6 is a flowchart showing medical image diagnosis support processing performed in the embodiment of the present disclosure. First, as shown in FIG. 6, the image reception unit 21 receives the target image selected by a user operating the input unit 15 (step ST1), and the display control unit 25 displays the received target image on the display unit (step ST2).

Next, the information reception unit 22 receives the information corresponding to the received target image (step ST3). In the present embodiment, information about an imaging part included in accessory information related to the target image is received as the information for recognizing each part of the target image.

Next, the extraction unit 23 extracts the analysis application corresponding to the received information based on the table T in FIG. 3 (step ST4), the activation unit 24 activates the extracted analysis application, and the display control unit 25 displays the extracted analysis application on the display unit 14 as shown in FIG. 4 (step ST5).

The display control unit 25 determines whether or not the result of analysis executed in the past by the activated analysis application exists for the target image (step ST6), and in a case where the result of analysis exists (step ST6; YES), the display control unit 25 acquires the result of analysis from the accessory information about the target image (step ST7). On the other hand, in a case where the result of analysis does not exist (step ST6; NO), the analysis in the analysis application activated by the activation unit 24 is executed (step ST8).

Next, the display control unit 25 displays the result of analysis executed in the past or the result of analysis executed by the analysis application on the screen 20 of the display unit 14 as shown in FIG. 5 (step ST9). The display control unit 25 determines whether or not all the results of analysis of the activated analysis application are displayed (step ST10), and in a case where not all the results of analysis are displayed (step ST110; NO), processing shifts to step ST6, and the display control unit 25 determines whether or not the result of analysis executed in the past by the next analysis application exists for the target image, and performs shift processing.

On the other hand, in step ST10, in a case where the display control unit 25 determines that all the results of analysis of the activated analysis application are displayed (step ST10; YES), the CPU 11 ends the series of processing.

As described above, according to the present embodiment, the analysis application corresponding to the target image is automatically extracted and activated only by a user selecting the target image for which image diagnosis is desired. Therefore, it is possible to save time and effort of finding the analysis application to be activated by a user, and it is possible to prevent a user from failing to select the necessary analysis application, and thus, it is possible to prevent the workflow from being degraded.

According to the present embodiment, in a case where the result of analysis executed in the past by the activated analysis application exists for the target image, the result of analysis in the past is displayed without performing analysis. Therefore, the time required for analysis can be shortened.

In the embodiment, the information reception unit 22 receives the information about the imaging part included in the accessory information related to the target image as the information for recognizing each part of the target image, but the technique of the present disclosure is not limited to this. For example, in a case where the target image is a heart image, a user right-clicks the mouse as the input unit 15 on a calcified region in the image to designate the calcified region of a heart region as an ROI, and the information reception unit 22 may receive pixel data (pixel value) of the designated ROI. In this case, based on the pixel data, the ROI is determined to be a "calcified region" in consideration of a position of the ROI, a signal value of the ROI, and a size of a high signal value region. In addition, the information reception unit 22 determines whether the target image is a non-contrast image or a contrast image based on use contrast agent information included in the accessory information related to the target image, and in a case where the target image is a non-contrast image, the extraction unit 23 may extract a calcification score calculation application, and in a case where the target image is a contrast image, the extraction unit 23 may extract a coronary artery analysis application. The extraction unit 23 can extract the analysis application based on the ROI information designated by a user, that is, the information indicating the designated region in the target image.

In the embodiment, the display control unit 25 displays the information indicating the analysis application activated by the activation unit 24 on the display unit 14, but the display control unit 25 may display the information indicating the analysis application extracted by the extraction unit 23 on the display unit 14. In a case where a plurality of the analysis applications are extracted by the extraction unit 23, the display control unit 25 displays, on the display unit 14, the information indicating a predetermined number of applications selected from the plurality of analysis applications based on priorities. In this case, as an example, the priorities can be determined in descending order of frequency of use in the analysis unit 30.

In the above-described embodiment, for example, as a hardware structure of a processing unit that executes various kinds of processing, such as the image reception unit 21, the information reception unit 22, the extraction unit 23, the activation unit 24, and the display control unit 25, various processors shown below can be used. As described above, the various processors include, in addition to the CPU that is a general-purpose processor that executes software (program) to function as various processing units, a programmable logic device (PLD) that is a processor capable of changing a circuit configuration after manufacture, such as a field programmable gate array (FPGA), and an exclusive electric circuit that is a processor having a circuit configuration exclusively designed to execute specific processing, such as an application specific integrated circuit (ASIC).

One processing unit may be constituted by one of these various processors, or may be a combination of two or more processors of the same type or different types (for example, a combination of a plurality of FPGAs or a combination of a CPU and an FPGA). In addition, a plurality of processing units may be constituted by one processor.

As an example in which the plurality of processing units are constituted by one processor, first, as represented by a computer such as a client and a server, one processor is constituted by a combination of one or more CPUs and software and this processor functions as the plurality of processing units. Second, as represented by a system on chip (SoC), a processor that realizes the functions of the entire system including the plurality of processing units by using one integrated circuit (IC) chip is used. As described above, the various processing units are constituted by using one or more of the various processors described above as a hardware structure.

Further, as the hardware structure of these various processors, more specifically, an electric circuit (circuitry) in which circuit elements such as semiconductor elements are combined can be used.

The disclosure of JP2018-182734 filed on Sep. 27, 2018 is incorporated herein by reference in its entirety.

All documents, patent applications, and technical standards described in this specification are herein incorporated by reference to the same extent that each individual document, patent application, or technical standard was specifically and individually indicated to be incorporated by reference.

What is claimed is:

1. A medical image diagnosis support device comprising a processor configured to:
   receive an image;
   receive information corresponding to the image;
   extract one or more analysis applications that correspond to the received information and display the one or more analysis applications on a display unit;
   activate at least one of the one or more analysis applications;
   access a storage device to determine whether a result of an analysis executed in the past by the activated analysis application exists for the received image;
   in a case where the result of the analysis executed in the past by the activated analysis application exists for the received image, display the result of the analysis executed in the past by the activated analysis application on the display unit without executing a new analysis on the received image by the activated analysis application; and
   in a case where the result of the analysis executed in the past by the activated analysis application does not exist for the received image, execute an analysis on the received medical image by the activated analysis application and display a result of the analysis on the display unit.

2. The medical image diagnosis support device according to claim 1,
   wherein the processor is configured to display a result of analysis executed by the activated analysis application activated on the display unit.

3. The medical image diagnosis support device according to claim 1,
   wherein the processor is configured to display information indicating the activated analysis application on the display unit.

4. The medical image diagnosis support device according to claim 1,
   wherein the processor is configured to display information indicating the one or more analysis applications on the display unit.

5. The medical image diagnosis support device according to claim 4,
   wherein, in a case where a plurality of the analysis applications are extracted, the processor is configured to display, on the display unit, information indicating an analysis application selected from the plurality of analysis applications based on priorities.

6. The medical image diagnosis support device according to claim 1,
   wherein, in a case where a plurality of the analysis applications are extracted, the processor is configured to activate an analysis application selected from the plurality of analysis applications based on priorities.

7. The medical image diagnosis support device according to claim 1,
   wherein the information includes at least one of information indicating a designated region in a reception image which is the received image, information for recognizing each part of the reception image, information for recognizing each organ region of the reception image, DICOM tag information, or information about a past report.

8. The medical image diagnosis support device according to claim 1,
   wherein in a case where an input instruction is made on a reception image which is the received image, the processor is configured to extract the analysis application based on information about the reception image on which the input instruction is made, and in a case where an input instruction is made on a designated region in the reception image, the processor is configured to extract the analysis application based on information about a part in the designated region.

9. The medical image diagnosis support device according to claim 1,
   wherein the image is a medical image.

10. A medical image diagnosis support method comprising:
    receiving an image;
    receiving information corresponding to the received image;
    extracting one or more analysis applications that correspond the received information and displaying the one or more analysis application on a display unit;
    activating at least one of the one or more analysis applications;
    accessing a storage device to determine whether a result of an analysis executed in the past by the activated analysis application exists for the received image;
    in a case where the result of the analysis executed in the past by the activated analysis application exists for the received image, displaying the result of the analysis on the display unit without executing a new analysis on the received image by the activated analysis application; and
    in a case where the result of the analysis executed in the past by the activated analysis application does not exist for the received image, executing an analysis on the received medical image by the activated analysis application and displaying a result of the analysis on the display unit.

11. A non-transitory computer-readable storage medium storing therein a medical image diagnosis support program causing a computer to execute:
    a procedure of receiving an image,
    a procedure of receiving information corresponding to the received image,
    a procedure of extracting one or more analysis applications that correspond to the received information and displaying the one or more analysis applications on a display unit,
    a procedure of activating at least one of the one or more analysis applications,
    a procedure of accessing a storage device to determine whether a result of an analysis executed in the past by the activated analysis application exists for the received image,
    a procedure of displaying the result of the analysis on the display unit without executing a new analysis on the received image by the activated analysis application, in a case where the result of analysis executed in the past by the activated analysis application exists for the received image, and
    a procedure of executing an analysis on the received medical image by the activated analysis application and displaying a result of the analysis on the display unit, in a case where the result of the analysis executed in the past by the activated analysis application does not exist for the received image.

* * * * *